US012721865B2

(12) United States Patent
Brown

(10) Patent No.: US 12,721,865 B2
(45) Date of Patent: Sep. 1, 2026

(54) METHOD FOR ADMINISTERING AN ANTIMICROBIAL TREATMENT TO AN ANIMAL IN A MEAT PROCESSING OPERATION

(71) Applicant: CARGILL, INCORPORATED, Wayzata, MN (US)

(72) Inventor: Tyson Brown, Godley, TX (US)

(73) Assignee: CARGILL, INCORPORATED, Wayzata, MN (US)

( * ) Notice: Subject to any disclaimer, the term of this patent is extended or adjusted under 35 U.S.C. 154(b) by 46 days.

(21) Appl. No.: 18/703,164

(22) PCT Filed: Oct. 20, 2022

(86) PCT No.: PCT/US2022/078402
§ 371 (c)(1),
(2) Date: Apr. 19, 2024

(87) PCT Pub. No.: WO2023/070014
PCT Pub. Date: Apr. 27, 2023

(65) Prior Publication Data

US 2025/0222023 A1 Jul. 10, 2025

Related U.S. Application Data

(60) Provisional application No. 63/257,676, filed on Oct. 20, 2021.

(51) Int. Cl.

| | |
|---|---|
| ***A61K 33/00*** | (2006.01) |
| ***A22B 3/02*** | (2006.01) |
| ***A61K 31/19*** | (2006.01) |
| ***A61K 31/194*** | (2006.01) |
| ***A61K 31/4166*** | (2006.01) |
| ***A61K 31/44*** | (2006.01) |
| ***A61K 31/4425*** | (2006.01) |
| ***A61K 33/04*** | (2006.01) |
| ***A61K 33/14*** | (2006.01) |
| ***A61K 33/20*** | (2006.01) |
| ***A61K 33/34*** | (2006.01) |
| ***A61K 33/40*** | (2006.01) |

(52) U.S. Cl.
CPC ................ *A61K 33/14* (2013.01); *A22B 3/02* (2013.01); *A61K 31/19* (2013.01); *A61K 31/194* (2013.01); *A61K 31/4166* (2013.01); *A61K 31/44* (2013.01); *A61K 31/4425* (2013.01); *A61K 33/04* (2013.01); *A61K 33/20* (2013.01); *A61K 33/34* (2013.01); *A61K 33/40* (2013.01)

(58) Field of Classification Search
CPC ..................................................... A61K 33/14
USPC .......................................................... 452/57
See application file for complete search history.

(56) References Cited

U.S. PATENT DOCUMENTS

| | | | | |
|---|---|---|---|---|
| 3,068,601 | A | 12/1962 | Arrowsmith | |
| 4,575,900 | A | 3/1986 | Hamel | |
| 5,112,270 | A | 5/1992 | Howard et al. | |
| 5,692,951 | A | 12/1997 | Huff | |
| 6,135,871 | A | 10/2000 | Jones | |
| 9,044,028 | B2 | 6/2015 | Evans | |
| 2004/0115322 | A1 | 6/2004 | Osborn | |
| 2004/0209562 | A1 | 10/2004 | Jones | |
| 2005/0181720 | A1 | 8/2005 | Osborn | |
| 2007/0141974 | A1* | 6/2007 | McNaughton | A23B 2/771 452/176 |
| 2018/0064119 | A1* | 3/2018 | Johnsen | A22B 5/0029 |

FOREIGN PATENT DOCUMENTS

| | | | |
|---|---|---|---|
| CN | 101115392 | A | 1/2008 |
| CN | 101321462 | A | 12/2008 |
| CN | 102669502 | A | 9/2012 |

OTHER PUBLICATIONS

Buncic et al, “Spread of microbial contamination associated with penetrative captive bolt stunning of food animals”, Food Control 13 (2002) 425-430.

FSIS Directive 7120.1, Rev. 55, “Safe and Suitable Ingredients Used in the Production of Meat, Poultry, and Egg Products”, Feb. 2021.

Grandin, “Recommended Captive Bolt Stunning Techniques for Cattle”, Department of Animal Science Colorado State University, Feb. 2020.

* cited by examiner

*Primary Examiner* — Richard T Price, Jr.

(57) ABSTRACT

An antimicrobial treatment is administered to an animal in a meat processing operation by stunning an animal by striking a site on an animal skull with a device having a percussive head configured to deliver a concussive blow to the site, and applying an antimicrobial treatment composition to the site before, during or after delivering the concussive blow to the site. In an aspect, an antimicrobial treatment is administered to the lymphatic system of an animal in a meat processing operation by stunning an animal by striking a site on an animal skull with a device having a percussive head configured to deliver a concussive blow to the site, and applying an antimicrobial treatment composition to the site before, during or after delivering the concussive blow to the site.

20 Claims, No Drawings

METHOD FOR ADMINISTERING AN ANTIMICROBIAL TREATMENT TO AN ANIMAL IN A MEAT PROCESSING OPERATION

CROSS-REFERENCE TO RELATED APPLICATIONS

This application is a national phase application of PCT Application No. PCT/US2022/078402, filed 20 Oct. 2022, which claims the benefit of U.S. Provisional Patent Application No. 63/257,676, filed 20 Oct. 2021, each of which is incorporated by reference in its entirety.

FIELD

The present invention relates to administering an antimicrobial treatment to an animal. More specifically, the present application relates to administering an antimicrobial treatment to an animal in a meat processing operation.

BACKGROUND

The presence of pathogens in meat is of real concern, because of the possibility of pathogen related illness and death in consumers of tainted products. Various steps have been taken over the years in commercial meat processing facilities to reduce the amount of pathogens on the surface of meat for this reason. See, for example, US Patent Application Publication No. US 2005/0181720, which describes a method of reducing microbial level on the carcass of an animal by applying a first antimicrobial agent to the animal hide and reducing moisture from the hide.

SUMMARY

In typical commercial meat processing operations, an animal is initially stunned and hung from a hook or hanger of a conveyor system, such as a trolley running along an overhead rail. The animal is then exsanguinated by severing the arteries at the base of the neck. The hide or feathers are then removed and the carcass is subjected to further processing steps to obtain meat products. As noted above, various surface treatment techniques have been employed for reducing the amount of pathogens on the surface of meat. However, these surface treatments do not address pathogens that are present internally in the animal at the time of harvest. Pathogens such as *Salmonella* may be present, for example, in the gut or the lymphatic system in an animal may contaminate the meat processed from the animal. For example, ground beef products may be contaminated when sourced from an animal having *Salmonella* present in lymph nodes.

In an aspect of the present disclosure, a method for administering an antimicrobial treatment to an animal in a meat processing operation comprises stunning an animal by striking a site on an animal skull with a device having a percussive head configured to deliver a concussive blow to the site, and applying an antimicrobial treatment composition to the site before, during or after delivering the concussive blow to the site. It has been found that the concussive blow at least penetrates the skin, and optionally penetrates the skull, of the animal, facilitating delivery of the antimicrobial treatment internally to the animal through the site of the concussive blow.

In an aspect of the present disclosure, a method for administering an antimicrobial treatment to the lymphatic system of an animal in a meat processing operation comprises stunning an animal by striking a site on an animal skull with a device having a percussive head configured to deliver a concussive blow to the site, and applying an antimicrobial treatment composition to the site before, during or after delivering the concussive blow to the site.

It has surprisingly been discovered that an antimicrobial that is applied to the site of a stunning concussive blow will be quickly transported into the brain through the stun wound and transported through the animal by the continued flow of body fluids through the circulatory system prior to expiration of the animal. While not being bound by theory, it is believed that because the heart continues to be active for a time after the animal has been stunned; the flow of fluids through the circulatory system delivers the antimicrobial to various tissues of the body, such as organs, muscles and components of the lymphatic system. While not being bound by theory, it is believed that the fluids of the circulatory system that deliver the antimicrobial include blood and/or lymph fluid.

In typical commercial meat processing operations, the time lapse between stun of the animal and ceasing of heart beat will occur in from 2 to 10 minutes. Likewise, the time lapse between stun of the animal and removal of the head of the animal is typically in less than 10 minutes. Thus, it is surprising that an antimicrobial can be delivered to various tissues of the body, such as organs, muscles and components of the lymphatic system, in the short time available under commercial meat processing conditions.

In an aspect, the present method delivers an antimicrobial to an organ of the animal. In an aspect, the present method delivers an antimicrobial to an organ selected from one or more of the liver, spleen, lung, heart and kidney.

In an aspect, the present method delivers an antimicrobial to muscle tissue of the animal.

In an aspect, the present method delivers an antimicrobial to lymphatic tissue of the animal. In an aspect, the present method delivers an antimicrobial to lymphatic tissue selected from one or more of lymphatic vessels, lymph nodes, lymphatic or lymphoid organs, and lymphoid tissues.

DETAILED DESCRIPTION

The aspects of the present invention described below are not intended to be exhaustive or to limit the invention to the precise forms disclosed in the following detailed description. Rather a purpose of the aspects chosen and described is by way of illustration or example, so that the appreciation and understanding by others skilled in the art of the general principles and practices of the present invention can be facilitated.

The present method may be applied to any animal that is harvested by a technique of initially stunning of the animal, followed by exsanguination prior to further processing. The present method is particularly advantageously applied in the production of red meat slaughter animals (i.e., an animal that is slaughtered for red meat consumption), including without limitation all age and classes of bovine, porcine, and ovine animals. Bovine animals include cattle, steers, heifers, cows, bulls, and also buffalo. Porcine animals include sows, gilts, barrows, boars, and feeder pigs. Ovine animals include sheep and lamb. Although portions of this application are directed toward the production of beef or beef carcasses, the present method is not necessarily limited to the production of beef products.

As noted above, the present method is carried out in conjunction with the step of stunning an animal during meat processing operation. Stunning is carried out by striking a site on an animal skull with a device having a percussive head configured to deliver a concussive blow to the site. Any suitable device for stunning may be used. Advantageously, the device is a power-assist device, such as a conventional animal slaughtering pistol that uses an explosive cartridge or a hydraulic or pneumatic driven mechanism to cause the instantaneous, temporary emergence of a solid or hollow cylindrical steel percussive head from the barrel. In an aspect, the device having a percussive head is a captive-bolt stunner. In an aspect, the device having a percussive head is a penetrative captive-bolt stunner. In an aspect, the device having a percussive head is a non-penetrative captive-bolt stunner.

In an aspect, it has been found the use of a device that is a penetrative captive-bolt stunner provides an advantage, in that because the bolt perforates the skull, the antimicrobial treatment composition is more easily transported inside the animal with ready access to the fluids of the circulatory system.

In an aspect, the device has a flat or convex "knocker head," to deliver an effective concussive force to stun the animal.

Various examples of stunning pistols having impact or knocker heads that extend beyond the muzzle of the device are described in U.S. Pat. No. 3,068,601; US Published Application No. 2004/0209562; U.S. Pat. Nos. 6,135,871 4,575,900; US Published Application No. 2004/0209562; and U.S. Pat. Nos. 5,692,951, and 9,044,028, the disclosures of which are incorporated by reference herein.

Examples of commercially available stunning devices include the "CASH" Special Captive, and the CASH Poultry Killer .22 Cartridge Powered Tool, both from the Accles and Shelvoke Company in the UK. The "CASH" Special Captive bolt stunner is a pistol style trigger operated tool. The bolt of this tool extends 4¼ inches from muzzle.

In the method, an animal is stunned by striking a site on an animal skull with the device having a percussive head. Typically, the animal is stunned at the middle of the forehead in a manner known in the harvesting art in order to render the animal unconscious without causing pain.

The antimicrobial treatment composition is applied to the site in a manner to facilitate delivery of the antimicrobial treatment internally to the animal through the site of the concussive blow. In an aspect, the antimicrobial treatment composition is applied to the percussive head prior to delivering the concussive blow to the site on the animal skull. Upon delivering the concussive blow to the site, the antimicrobial treatment composition is delivered internally to the animal in a single step. In an aspect, the percussive head is configured with a reservoir to retain a dose of the antimicrobial treatment composition for delivery upon contact of the percussive head with the site. In an aspect, the antimicrobial treatment composition is applied to a removable sleeve configured to attach to the percussive head prior to delivering the concussive blow to the site on the animal skull.

In an aspect, the antimicrobial treatment composition is applied to the site on the animal skull before delivering the concussive blow to the site. In an aspect, the antimicrobial treatment composition is applied as a non-flowing composition to the site so that it remains in place prior to administration of the concussive blow In an aspect, the antimicrobial treatment composition is applied to the site on the animal skull after delivering the concussive blow to the site.

The antimicrobial treatment composition is applied to the percussive head or to the site (before or after delivering the concussive blow) by any appropriate technique. In an aspect, the antimicrobial treatment composition is applied by depositing an aliquot of the composition by a metered dose delivery device. In an aspect, the antimicrobial treatment composition is applied by depositing an aliquot of the composition by a syringe. In an aspect, the antimicrobial treatment composition is applied by depositing an aliquot of the composition by a spray device. In an aspect, the antimicrobial treatment composition is applied by depositing an aliquot of the composition by a swabbing device. In an aspect, the antimicrobial treatment composition is applied by depositing a viscous plug comprising the antimicrobial treatment composition. In an aspect, the antimicrobial treatment composition is applied by depositing a foam comprising the antimicrobial treatment composition. In an aspect, the antimicrobial treatment composition is applied by depositing a gel comprising the antimicrobial treatment composition. In an aspect, the antimicrobial treatment composition is applied as an aerosol comprising the antimicrobial treatment composition. In an aspect, the antimicrobial treatment composition is applied by depositing dissolvable composition comprising the antimicrobial treatment composition.

The antimicrobial treatment composition can include any additive known to kill or neutralize bacteria or other kinds of microbes. In an aspect, the antimicrobial treatment composition comprises any substance approved by the United States Department of Agriculture Food Safety and Inspection service for use as an antimicrobial treatment of meat, poultry and egg products. Listings of such materials are updated at https://www.fsis.usda.gov.

In an aspect, the antimicrobial treatment composition comprises a compound selected from the group consisting of acetic acid; acidified sodium chlorite; ammonium sulfate; calcium hypochlorite; cetylpyridinium chloride; chlorine; citric acid; copper sulfate; 1,3-dibromo-5,5 dimethylhydantoin (DBDMH); dipicolinic acid (DPA); hydrochloric acid; hydrogen peroxide (HP); 1-hydroxyethylidene-1,1-diphosphonic acid (HEDP); hypochlorous acid; octanoic acid; peroxyacetic acid (PAA); sodium hypochlorite; sodium sulfate; sulfuric acid; trisodium phosphate (TSP); lactic acid; and mixtures thereof.

In an aspect, the antimicrobial treatment composition comprises an antibiotic of natural origin produced by fungi and bacteria. In an aspect, the antimicrobial treatment composition comprises a semi-synthetic antibiotic. In an aspect, the antimicrobial treatment composition comprises a chemical compound produced via chemical synthesis. In an aspect, the antimicrobial treatment composition comprises an antibiotic selected from the group consisting of penicillin, streptomycin, oxacillin, amoxicillin, quinolones, and sulphonamides.

In an aspect, the antimicrobial treatment composition comprises an antibiotic selected to treat a microbe selected from *Salmonella, E. coli, Staphylococcus, Campylobacter, Listeria*, and *Clostridium*.

In an aspect, the antimicrobial treatment composition comprises a Bacteriophage.

In an aspect, the antimicrobial treatment composition is in the form of a liquid. In an aspect, the antimicrobial treatment composition is applied as composition having a viscosity of from about 50 to 250 cps at 23° C. (i.e., about the viscosity of corn syrup or maple syrup). In an aspect, the antimicrobial treatment composition is applied as composition having a viscosity of from about 250 to 4000 cps at 23° C. (i.e., about the viscosity of castor oil or honey). In an aspect, the antimicrobial treatment composition is applied as composition having a viscosity of from about 4000 to 10,000 cps at 23° C. (i.e., about the viscosity of molasses). In an aspect, the antimicrobial treatment composition is applied as composition having a viscosity of from about 10,000 to 35000 cps at 23° C. (i.e., about the viscosity of chocolate syrup). In an aspect, the antimicrobial treatment composition is applied as composition having a viscosity of from about 35,000 to 100,000 cps at 23° C. (i.e., about the viscosity of ketchup). In an aspect, the antimicrobial treatment composition is applied as composition having a viscosity of from about 100,000 to 500,000 cps at 23° C. (i.e., about the viscosity of peanut butter). In an aspect, the antimicrobial treatment composition is applied as composition having a viscosity of from about 500,000 to 2,000,000 cps at 23° C. (i.e., about the viscosity of lard). In an aspect, the antimicrobial treatment composition is applied as composition having a viscosity of from about 2,000,000 to 10,000,000 cps at 23° C. (i.e., about the viscosity of silicone sealant).

In an aspect, the antimicrobial treatment composition is in the form of a foam. In an aspect, the antimicrobial treatment composition is in the form of a paste. In an aspect, the antimicrobial treatment composition is in the form of a gel. In an aspect, the antimicrobial treatment composition is in the form of a dissolvable solid. In an aspect, the antimicrobial treatment composition is in the form of a dissolvable pellet.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. Examples of such limitations include preparing the sample in a wet versus a dry environment, different instruments, variations in sample height, and differing requirements in signal-to-noise/ratios. For example, "about" can mean greater or lesser than the value or range of values stated by 1/10 of the stated values, but is not intended to limit any value or range of values to only this broader definition. For instance, a concentration value of about 30% means a concentration between 27% and 33%. Each value or range of values preceded by the term "about" is also intended to encompass the embodiment of the stated absolute value or range of values. Alternatively, particularly with respect to biological systems or processes, the term can mean within an order of magnitude, preferably within 5-fold, and more preferably within 2-fold, of a value.

Throughout this specification and claims, unless the context requires otherwise, the word "comprise", and variations such as "comprises" and "comprising", will be understood to imply the inclusion of a stated integer or step or group of integers or steps but not the exclusion of any other integer or step or group of integer or step. When used herein "consisting of" excludes any element, step, or ingredient not specified in the claim element. When used herein, "consisting essentially of" does not exclude materials or steps that do not materially affect the basic and novel characteristics of the claim. In the present disclosure of various embodiments, any of the terms "comprising", "consisting essentially of" and "consisting of" used in the description of an embodiment may be replaced with either of the other two terms:

All patents, patent applications (including provisional applications), and publications cited herein are incorporated by reference as if individually incorporated for all purposes. Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for administering an antimicrobial treatment to an animal in a meat processing operation comprising:

stunning an animal by striking a site on an animal skull with a device having a percussive head configured to deliver a concussive blow to the site, and applying an antimicrobial treatment composition to the site before, during or after delivering the concussive blow to the site, wherein the antimicrobial treatment composition is delivered internally to the animal through the site of the concussive blow.

2. A method for administering an antimicrobial treatment to the lymphatic system of an animal in a meat processing operation comprising:

stunning an animal by striking a site on an animal skull with a device having a percussive head configured to deliver a concussive blow to the site, and applying an antimicrobial treatment composition to the site before, during or after delivering the concussive blow to the site, wherein the antimicrobial treatment composition is delivered internally to the animal through the site of the concussive blow.

3. The method of claim 1, wherein the antimicrobial treatment composition is applied to the percussive head prior to delivering the concussive blow to the site on the animal skull.

4. A method for administering an antimicrobial treatment to an animal in a meat processing operation comprising:

stunning an animal by striking a site on an animal skull with a device having a percussive head configured to deliver a concussive blow to the site, and applying an antimicrobial treatment composition to the site before, during or after delivering the concussive blow to the site, wherein the antimicrobial treatment composition is applied to a removable sleeve configured to attach to the percussive head prior to delivering the concussive blow to the site on the animal skull.

5. The method of claim 1, wherein the antimicrobial treatment composition is applied to the site on the animal skull after delivering the concussive blow to the site.

6. The method of claim 1, wherein the antimicrobial treatment composition is applied to the site on the animal skull before delivering the concussive blow to the site.

7. The method of claim 1, wherein the antimicrobial treatment composition is applied by depositing:

an aliquot of the composition by a metered dose delivery device, by a syringe, by a spray device, or by a swabbing device;

a viscous plug comprising the antimicrobial treatment composition;

a foam comprising the antimicrobial treatment composition; or a gel comprising the antimicrobial treatment composition.

8. The method of claim 1, wherein the antimicrobial treatment composition comprises a compound selected from the group consisting of acetic acid; acidified sodium chlorite; ammonium sulfate; calcium hypochlorite; cetylpyridinium chloride; chlorine; citric acid; copper sulfate; 1,3-dibromo-5,5 dimethylhydantoin (DBDMH); dipicolinic acid (DPA); hydrochloric acid; hydrogen peroxide (HP); 1-hydroxyethylidene-1,1-diphosphonic acid (HEDP); hypochlorous acid; octanoic acid; peroxyacetic acid (PAA); sodium hypochlorite; sodium sulfate; sulfuric acid; trisodium phosphate (TSP); lactic acid; and mixtures thereof.

9. The method of claim 1, wherein the antimicrobial treatment composition comprises: an antibiotic of natural origin produced by fungi and bacteria, a semi-synthetic antibiotic, or a chemical compound produced via chemical synthesis.

10. The method of claim 1, wherein the antimicrobial treatment composition comprises an antibiotic selected from the group consisting of penicillin, streptomycin, oxacillin, amoxicillin, quinolones, and sulphonamides.

11. The method of claim 1, wherein the antimicrobial treatment composition is in the form of a liquid.

12. The method of claim 1, wherein the antimicrobial treatment composition is in the form of a foam.

13. The method of claim 1, wherein the antimicrobial treatment composition is in the form of a paste.

14. The method of claim 1, wherein the antimicrobial treatment composition is in the form of a gel.

15. The method of claim 1, wherein the device having a percussive head is a captive-bolt stunner.

16. The method of claim 1, wherein the device having a percussive head is a penetrative captive-bolt stunner.

17. The method of claim 1, wherein the animal is selected from cattle, steers, heifers, cows, bulls, buffalo, sows, gilts, barrows, boars, feeder pigs, sheep and lamb.

18. The method of claim 1, wherein the antimicrobial is delivered to an organ of the animal selected from one or more of the liver, spleen, lung, heart and kidney.

19. The method of claim 1, wherein the antimicrobial is delivered to muscle tissue of the animal.

20. The method of claim 1, wherein the antimicrobial is delivered to lymphatic tissue of the animal.

* * * * *